United States Patent [19]

Nikoonahad et al.

[11] Patent Number: 5,576,831
[45] Date of Patent: Nov. 19, 1996

[54] WAFER ALIGNMENT SENSOR

[75] Inventors: Mehrdad Nikoonahad, Menlo Park; James A. Tebelskis, San Jose, both of Calif.

[73] Assignee: Tencor Instruments, Santa Clara, Calif.

[21] Appl. No.: 263,203

[22] Filed: Jun. 20, 1994

[51] Int. Cl.⁶ .................................................. G01B 11/00
[52] U.S. Cl. .......................... 356/375; 356/381; 356/237; 250/559.27; 250/559.31
[58] Field of Search ..................................... 356/371, 375, 356/376, 381, 237, 73; 250/559.27, 559.31, 559.41

[56] References Cited

U.S. PATENT DOCUMENTS

| | | | |
|---|---|---|---|
| 3,667,846 | 6/1972 | Nater et al. | 356/371 |
| 4,405,238 | 9/1983 | Grobman et al. | 356/401 |
| 4,589,773 | 5/1986 | Ido et al. | 356/371 |
| 4,650,983 | 3/1987 | Suwa | 250/204 |
| 4,748,333 | 5/1988 | Mizutani et al. | 250/561 |
| 4,844,617 | 7/1989 | Kelderman et al. | 356/372 |
| 4,864,123 | 9/1989 | Mizutani et al. | 250/225 |
| 4,936,676 | 6/1990 | Stauffer | 356/375 |
| 5,162,642 | 11/1992 | Akamatsu et al. | 356/376 |
| 5,166,516 | 11/1992 | Kajimura | 250/234 |
| 5,272,517 | 12/1993 | Tokura | 356/375 |
| 5,298,976 | 3/1994 | Shahar et al. | 356/375 |

Primary Examiner—F. L. Evans
Attorney, Agent, or Firm—Majestic, Parsons Siebert & Hsue

[57] ABSTRACT

A surface height detection and positioning device for use in a surface inspection system. An incident beam of light impinges obliquely upon the surface, and a position detector is disposed to receive light reflected from the surface. The position detector has a sensitivity characteristic graded along a direction transverse to the surface, so that the output of the position detector is used to determine a height of the surface. The device can be incorporated into a particle detection system that scans patterned wafers with obliquely incident light to search for particles with a particle detector positioned to receive scattered light. In one embodiment, the position detector can have a width that is graded along the direction transverse to the surface, so that a scan line on the surface that is focused upon the position detector crosses the width of that detector in a time that varies as a function of the height of the surface. This time can be measured as an electrical pulse from the position detector that can be used for various purposes, including adjusting the height of the surface during scanning. In another embodiment, the position detector can have a periodic variance in light sensitivity that is graded, so that varying a height of the surface varies a phase of the output from the position detector.

35 Claims, 7 Drawing Sheets

WAFER ALIGNMENT SENSOR

TECHNICAL FIELD

The present invention relates to a system for aligning a wafer or the like. In particular, the system facilitates optical detection of flaws and particles on a surface of a semiconductor wafer.

BACKGROUND ART

During the production of semiconductor wafers for integrated circuits (ICs), optical scanning for defects or contaminants on a surface of the wafers is common. Such scanning can involve focusing a beam of light to a spot on the surface and detecting whether the light is scattered, as opposed to being specularly reflected from that spot, thereby signaling the presence or absence of a foreign particle at that spot. It is often useful to perform contamination searches at various stages during such production.

It has been found that particle to background signal contrast can be optimized by directing the beam obliquely at the wafer surface. Each time a wafer is scanned, it is important that the surface is accurately positioned, in order that the scanning beam is focused on the surface and to ascertain the position on the surface of any particles or defects. This is especially true for scanning with an oblique beam of light, for which case a slight change in height or tilt of the wafer surface can lead to a large error in the position on the wafer surface.

In U.S. Pat. No. 5,272,517, Tokura teaches a height measurement apparatus in which a laser light beam is directed normally toward a surface to reflect from an inclined feature, such as a solder flow, connecting an IC with a printed circuit board (PCB). The light reflected from the solder flow is collected at a detector in order to estimate the height of the IC from the PCB.

U.S. Pat. No. 5,166,516 to Kajimura teaches a slant detection and control mechanism for a scanning probe microscope in which a light beam is reflected off a back surface of a cantilevered beam having a probe on a front surface. The reflected beam undergoes multiple reflections to arrive at a detector that determines the deflection of the probe toward an object being scanned.

In U.S. Pat. Nos. 4,748,333, Mizutani et al. teach a surface displacement sensor having multiple slits and lenses aligned along a trajectory of light reflecting from the surface at an oblique angle, and a sensor positioned at an end of that trajectory which receives increased light when the slits are aligned with the light. At least one of the slits can be narrowed for increasing the accuracy of the surface displacement.

U.S. Pat. No. 4,864,123 to Mizutani et al. also utilizes the alignment of multiple slits and lenses along a trajectory of light that is obliquely reflected off a surface to determine the level of that surface. This patent teaches the advantage of polarization correcting optics for adjusting the intensity ratio between orthogonal polarized components of the reflected light.

It is an object of the present invention to devise an accurate measurement of surface height for a wafer inspection system.

It is another object of the present invention that the measurement of the surface height is accomplished with the same source of light that is used for particle inspection of the system.

It is yet another object of the present system to provide means for using the measurement of the surface height to adjust a position of the surface during particle inspection.

SUMMARY OF THE INVENTION

The above objects are accomplished with a wafer surface alignment system that utilizes specular reflection from an obliquely incident beam of light, the specularly reflected light being detected by a sensor having a graded sensitivity. This beam of incident light can be the same beam that is used to detect particles on the wafer surface by scanning the surface and detecting scattered light.

The incident beam of light impinges upon a wafer surface, typically at a small angle to that surface, and reflects from the surface at a similar angle. A focussing lens or mirror is positioned in the path of that reflected light, focusing the light at an image plane, where a light sensitive position detector is disposed. The position detector has a sensitivity that is graded in a direction transverse to the surface, so that an electrical signal output from the position detector carries information about the distance along the graded direction at which the reflected beam impinges upon the position detector. This information can relate to the amplitude, duration or phase of the output signal. This distance is in turn related to a height and tilt of the surface, and information regarding the height and tilt, which is referred to collectively as an "effective height," can be used to better position the surface for wafer inspection or to correct a location on the surface at which a particle is detected.

The wafer alignment system can augment an existing particle detection system that scans a wafer surface with obliquely incident light to detect scattered light. In such a system, the incident beam scans across the surface in a series of lines that are generally normal to the incident beam. The length of a reflected image of the scan lines in time or distance can be used to determine the alignment of the wafer surface by employing a position detector having a width that increases along a direction transverse to the image of the scan lines. For example, a position detector having a graded sensitivity can be made from a wedge shaped detection surface. Similarly, such a position detector can be made having a plate with a wedge shaped aperture adjoining the detection surface that intercepts a portion of the reflected scan line. Since the length of the reflected scan line detected varies in either of these situations in a graded fashion along the wedges, the output of the detector is proportional to the effective height of the surface. This can be measured as a duration of an electrical pulse generated by the detector during a scan.

Other types of position detectors having a graded sensitivity may alternatively be employed. For example, a partly translucent filter may be disposed between a detector having a uniform sensitivity and the reflected light, the filter having a graded translucence. The detector may instead be a photodetector formed of a p-n junction that has a graded concentration of dopants, thereby having an output voltage or current that varies, for a given intensity of light impinging upon the detector, depending upon the position of the light on the detector.

The scanning of the wafer surface for particles may be accomplished with a beam of light that is directed along a fixed trajectory, but is deflected along a horizontal y-axis direction by an acousto-optic deflector (AOD) or a mechanical device such as a resonant or polygon scanner. With any of these devices, each scan period corresponds to a scan of the surface along the y-axis direction. A servo controlled positioning system moves the wafer surface along a horizontal x-axis direction as the beam scans in the y-axis direction, such that many scans along the y-axis direction are performed during a single sweep of the wafer surface in the x-axis direction. During each scan in the y-axis direction, information about the effective height of the wafer surface is collected by the position detector so that a vertical z-axis position of the wafer surface can be measured and adjusted by the positioning system for a subsequent scan.

For wafer surfaces that have been patterned with ICs, the optical reflectivity of the surface can vary over several orders of magnitude, due to both variations in the reflectivity of the materials forming the pattern and interference effects due to local height or reflectivity variations. To remove intensity variations at the position detector due to these reflectivity variations, a reference detector is employed that does not have a graded sensitivity, and a beam splitter is positioned in the path of the reflected light to divert a portion of the reflected light toward the reference detector. A spatial filter can also be employed near a Fourier transform plane of the lens to remove all but the zero order diffraction of the reflected light.

Another embodiment employs a position sensor with a periodic variation in sensitivity that varies in phase along a direction that the image varies due to a change in wafer surface height. This phase change may be detected, for example, by comparison with a reference sensor having a periodic sensitivity that does not change in phase along with changes in image height. Due to an increase in the number of signals due to the periodic variations, an improved accuracy may be achieved with this device. It is also possible to combine this position sensor with those previously described, creating a sensor that varies in both sensitivity and phase along a direction that the image varies with a change in wafer surface height.

BEST MODE FOR CARRYING OUT THE INVENTION

Figure 1:
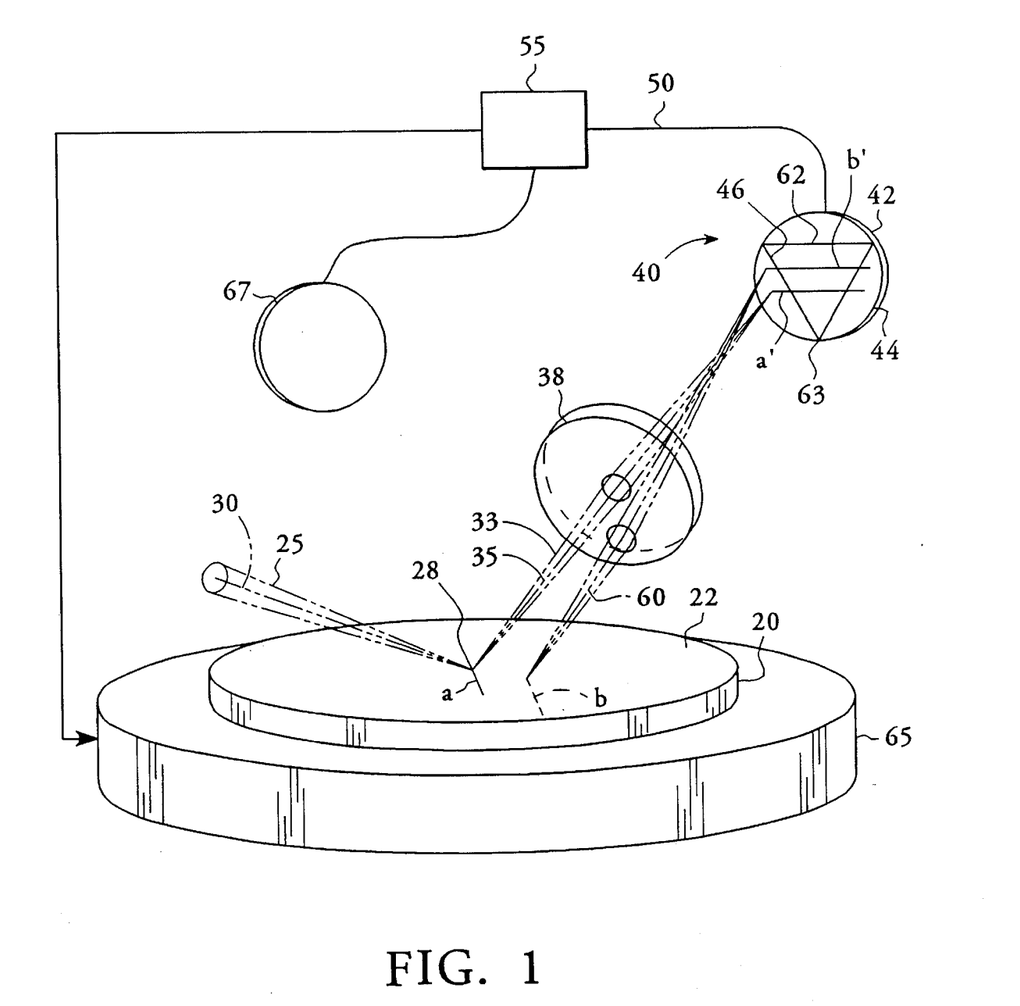
FIG. 1 is a diagram of a surface positioning system of the present invention for particle detection on an unpatterned surface.

Referring now to FIG. 1, a diagram of a position sensor for an unpatterned wafer 20 having a surface 22 shows an obliquely incident beam of light 25 being focused on a spot 28 on the surface 22. The incident beam 25, which may be produced by a laser 26, is centered about an axis 30 that is preferably in a range of between 55° and 85° from normal to the wafer surface. The incident beam 25 is primarily reflected from the spot 28 as a reflected beam 33 centered about an axis 35 oriented generally at an equal and opposite angle from normal to the wafer surface as the incident beam axis 30. While searching for particles on the surface 22 a scanning device 31 is utilized to cause, the incident beam 25 to repeatedly scan portions of the surface, such as line (a), which represents one such small scan line, an end of which coincides with spot 28. Scan line (a) may have a length of about 3 mm to about 30 mm in the length variable depending upon the application desired.

The reflected beam 33 diverges from a focused "waist" at the spot 28 that may range from less than 1 μm to 100 μm, depending upon the application. The divergence of the reflected beam 33 may be due to both a defocusing of the incident beam 25 beyond the waist and due to some roughness of the surface 22 that causes imperfect reflection.

Due to the divergence of the reflected beam 33 from the spot 28 a focusing lens 38 is placed in the path of the reflected beam 33. The lens 38 has a focal length f and is positioned from the spot a distance greater than f in order to focus the light from the spot 28. In the preferred embodiment the lens 38 is located a distance of about $2f$ from the spot 28, as this distance allows for small errors in focusing yet is not so large as to be cumbersome. The lens 38 is formed of a sandwich of two thin lenses having different indices of refraction selected to remove chromatic aberration of the reflected beam. At an opposite side of the lens 38 from the spot, and disposed at an approximately equal distance from the lens 38 as the distance between the lens 38 and the spot 28, is a position detector 40. The position detector is therefore located near an image plane of the spot 28 and the scan line (a).

The position detector 40 of this embodiment is comprised of a photodetector 42 adjoined by a plate 44 that defines a V-shaped aperture 46. The V-shaped aperture 46 may be positioned approximately at the image plane and the photodetector 42 spaced slightly behind the image plane, in order to blur an image of the spot 28 to smooth local non-uniformities in sensitivity that may be present in the photodetector. An image of the scan line (a) from the surface 22 is shown as a line (a') on the position detector 40. Due to the V-shaped aperture, only a central portion of the light of image line (a') impinges upon the photodetector 42. In response to that portion of the light impinging upon the photodetector 42, an electrical signal is sent by the photodetector 42 along lead 50 to a signal processing unit 55. The portion of line (a') that traverses the aperture 46 and is received by the photodetector 42 creates an electrical pulse that is of equal or lesser duration than the time required for the incident beam to travel the length of image line (a). Since the portion of the scan line image (a') that is received by the photodetector 42 depends upon the position at which the line (a') scans across the position detector 40, the duration of the electrical pulse sent on lead 50 is a function of the location of image line (a') on the position detector 40.

The duration of the pulse can thus be used to determine the effective height of the surface 22 relative to a desired height. If, for example, the surface has too low an effective height, then instead of scanning the surface 22 along line (a), incident beam 25 will instead scan the surface 22 along scan line (b) and be reflected from the surface 22 along reflected beam 60. After passing through lens 38, reflected beam 60 will be focused at the position detector 40, with image line (b') representing an image of scan line (b). Due to the low effective height of surface 22, image line (b') intercepts the V-shaped aperture 46 near a top 62 of the aperture 46 than image line (a'). For this reason, almost all of image line (b') impinges upon photodetector 42, creating a longer pulse. Similarly, although not shown in this illustration, a surface 22 which is too high would produce a shorter pulse than that produced by image line (a'), as an image of a scan line in that case would intercept the position detector near a nadir 63 of the V-shaped aperture, so that nearly the full scan line image would impinge upon the photodetector 42.

The duration of the pulse received from the lead 50 is measured by the signal processing circuitry 55, which determines leading and trailing edges of each pulse by signaling when the voltage is above a set voltage level. Based upon a comparison of the measured pulse length and a reference pulse length, the signal processing circuitry 55 can send a signal to a servo controlled stage 65 that holds the wafer 20, the stage 65 thereby adjusting the height of the wafer 20 such that the surface 22 is in a preferred position.

Other types of position detectors 40 may alternatively be employed. For example, the photodetector 42 may itself be V-shaped, eliminating the need for a V-shaped aperture 46. Or the photodetector 42 may have a uniform sensitivity and width but have a filter with a graded translucence covering the photodetector. On the other hand, the photodetector 42 may have a uniform width but a graded sensitivity, as can be produced by doping a PIN junction of the photodetector with a graded concentration of dopants.

A particle detector 67 is disposed at a position above the surface 22 and spaced apart from both the incident beam 25 and the reflected beam 33. The particle detector 67 has a photodetective sensor that detects light scattered by a particle on the surface 22. The particle detector 67 is connected with the signal processing circuitry 55 which correlates the detection of scattered light with a location of the spot 28 at the time of the detection of the scattered light, in order to determine where on the surface 22 a particle exists.

Figure 2:
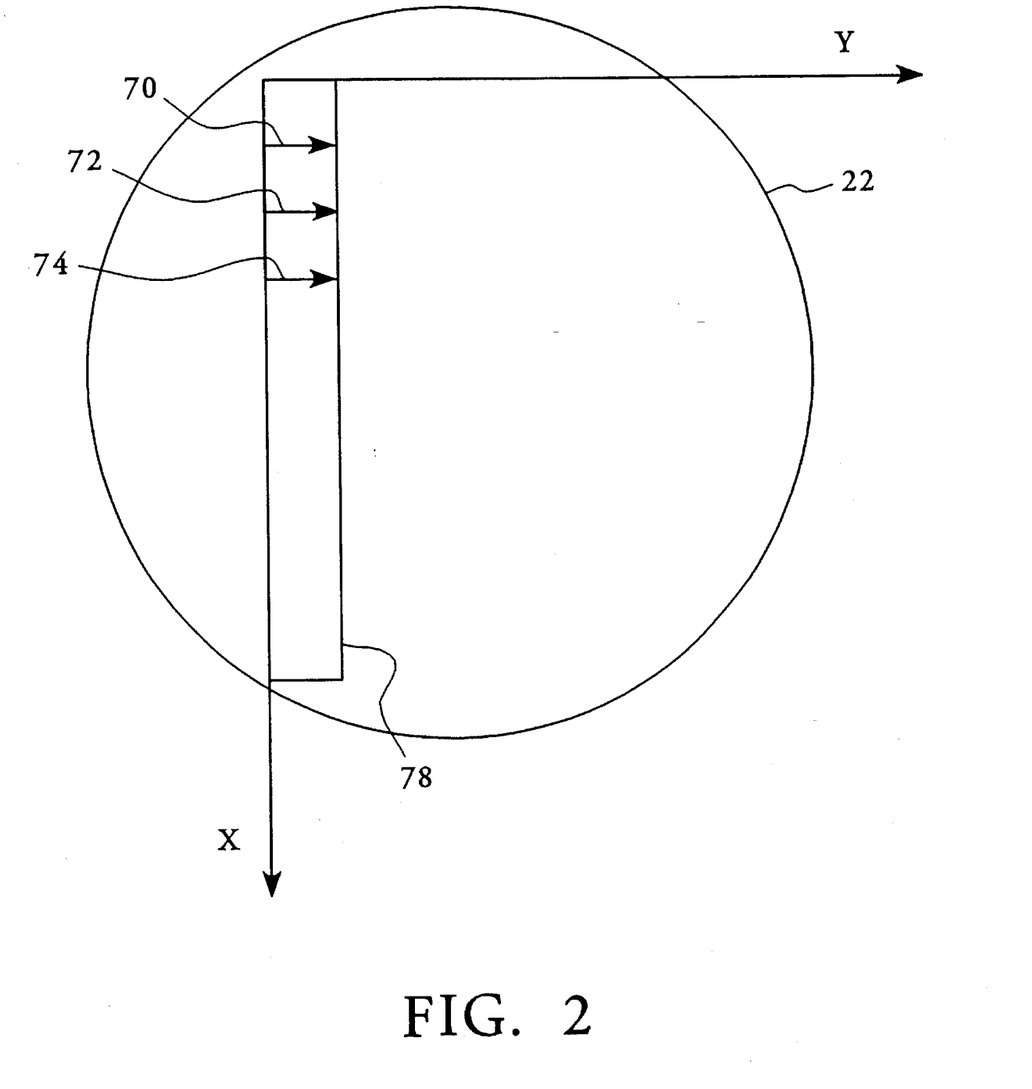
FIG. 2 is a top view of a scanning sequence on the surface of FIG. 1.

FIG. 2 shows a top view of the scanning of a wafer surface 22 by an incident beam, not shown, that is oriented generally along the x and z directions, the z direction pointing out of the plane of the paper. The beam scans across the wafer surface along the y direction in individual scan lines 70, 72 and 74 that have a length that is a fraction of a diameter of that wafer 20. The scanning may be produced by an AOD or mechanical device over a wide range of frequencies, from less than 100 Hz to nearly 100 kHz. Faster or slower scanning frequencies may be employed, depending upon a tradeoff between particle sensitivity and wafer throughput. As the beam scans back and forth in the y direction, the wafer is moved along the x direction by the servo controlled stage 65, which is not shown in this figure. Although the scan lines 70, 72 and 74 are shown spaced apart for ease of illustration, actual scan lines would be much closer together. After the wafer surface 22 has been moved along the x direction so that the scan lines have swept across a strip 78 having a width equal to the length of the scan lines and a length spanning the surface along the x direction, the wafer surface 22 is moved a distance in the y direction approximately equal to the length of a scan line, and a similar strip adjoining strip 78 is scanned. In this fashion the entire surface 22 is scanned with light.

Referring additionally to FIG. 1, the reflected image of a scan line 72 is received by the position detector 40, which sends an electrical pulse to the signal processing circuitry 55. Depending upon the length of the pulse received by the signal processing circuitry 55, that circuitry can cause the stage 65 to raise or lower the wafer surface 22 for a subsequent scan 74. Thus the system of FIGS. 1 and 2 automatically positions a wafer surface 22 at a preferred height while the surface 22 is being scanned.

Figure 3:
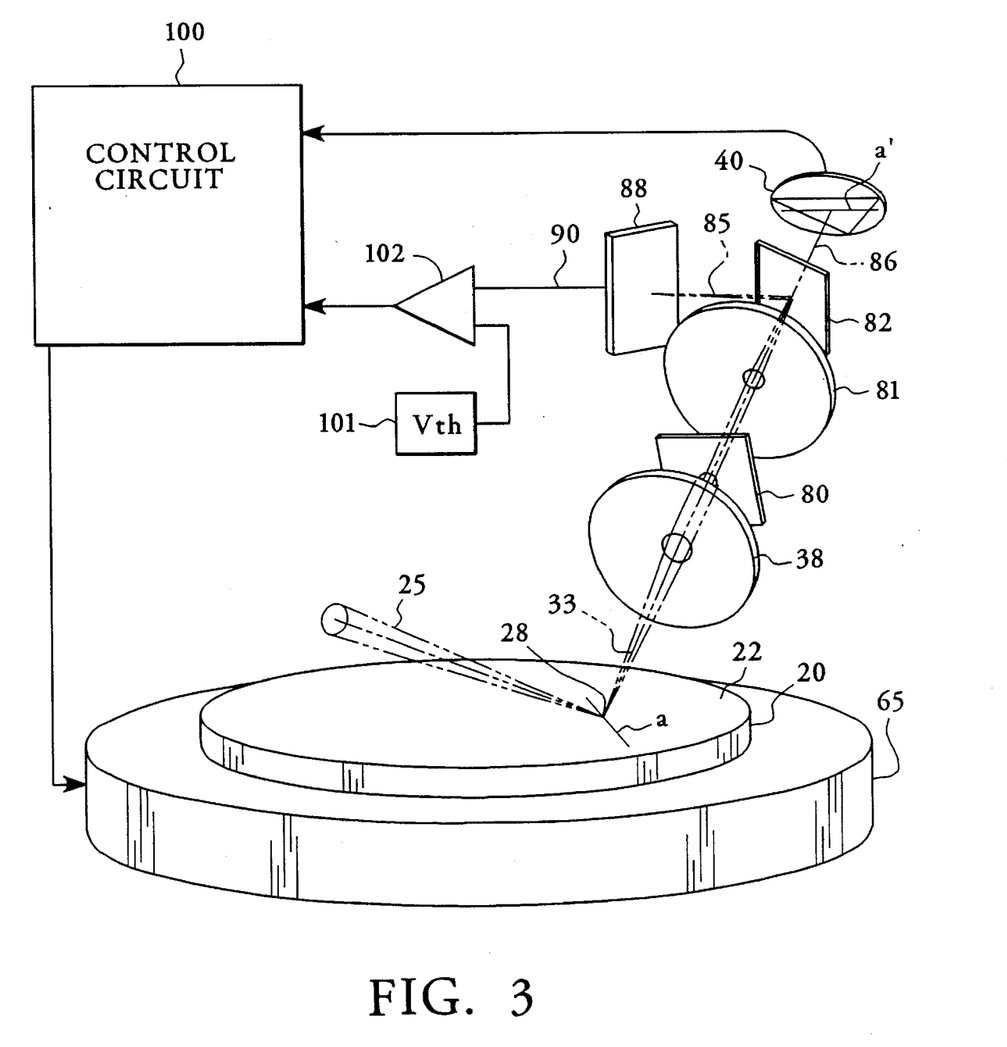
FIG. 3 is a diagram of a surface positioning system for patterned wafers.

FIG. 3 shows a dual lens, intensity normalized embodiment of the present invention which is preferred for a wafer having a patterned or inhomogenous surface 22. As before, an incident beam 25 is shown reflecting obliquely from the surface 22 along scan line (a) as a reflected beam 33. In this embodiment, however, a lens 38 is positioned a distance from the spot 28 where the incident beam 25 reflects from the surface that is approximately equal to the focal length f of the lens 38, so that the diverging light of reflected beam 33 is transformed into parallel rays by the lens 38. At a Fourier transform plane located a distance f on the opposite side of the lens 38 from the spot 28 a spatial filter 80 is positioned, and at a distance f on the opposite side of that filter 80 from the lens 38 a second lens 81 is disposed. The spatial filter 80 positioned at the Fourier transform plane removes higher order diffraction patterns from the patterned surface 22, while allowing specularly reflected or zero order diffracted light to pass through essentially unperturbed. The second lens 81, which also has a focal length f, focuses the parallel rays of the beam 33 that pass through the spatial filter 80 onto a position detector 40 located a distance f on the opposite side of the second lens 81 from the filter 80. Thus, an image (a') of the scan line (a) is received at the position detector.

A beam splitter 82 is disposed between the second lens 81 and the position detector 40. The beam splitter 82 may be made of a thin plate of polished glass or other partially reflective material having parallel surfaces obliquely angled to the reflected beam 33, so that a part 85 of the beam 33 is diverted to a reference detector 88 while another part 86 of the beam 33 continues to impinge upon the position detector 40. The reference detector 88, unlike the position detector 40, does not have a graded light sensitivity but instead has a uniform light sensitivity. When variations in the reflectivity of the surface 22 cause a variation in the intensity of the reflected beam 33, that variation is detected via the beam part 85 by a reference signal sent along lead 90 from the reference sensor 88. By comparing a ratio of the reference signal with the signal from the position detector 40, a normalized signal from the position detector 40 may be obtained that is not adversely affected by variations in the intensity of the reflected beam 33, although that intensity may range over four orders of magnitude. It should be noted that the beam splitter 82 can be disposed between the spatial filter 80 and the second lens 81, rather than between the second lens 81 and the position detector 40, but this would require a third lens to focus the light diverted toward the reference detector 88.

Both the signal from the position detector 40 and the signal from the reference detector 88 are input to a control circuit 100. Control circuit 100 compares the signal from the position detector 40 with that from the reference detector 88, to determine whether the signal from the position detector 40 is a set fraction of that from the reference detector 88. Signals from the position detector 40 that are above this fraction of the signal from the reference detector 88 thus represent a pulse from position detector 40, the length of which corresponds to the effective height of the surface 22. A threshold level 101 for the reference signal is set by a comparator 102 to be below the signal levels from the low end of the intensity range of the reflected beam 33, so that optical noise is filtered out. For signals above that threshold level, the control circuit 100 responds to the pulse length from the position detector 40 by sending instructions to the stage 65 which are used to control the effective height of the surface 22.

Figure 4:
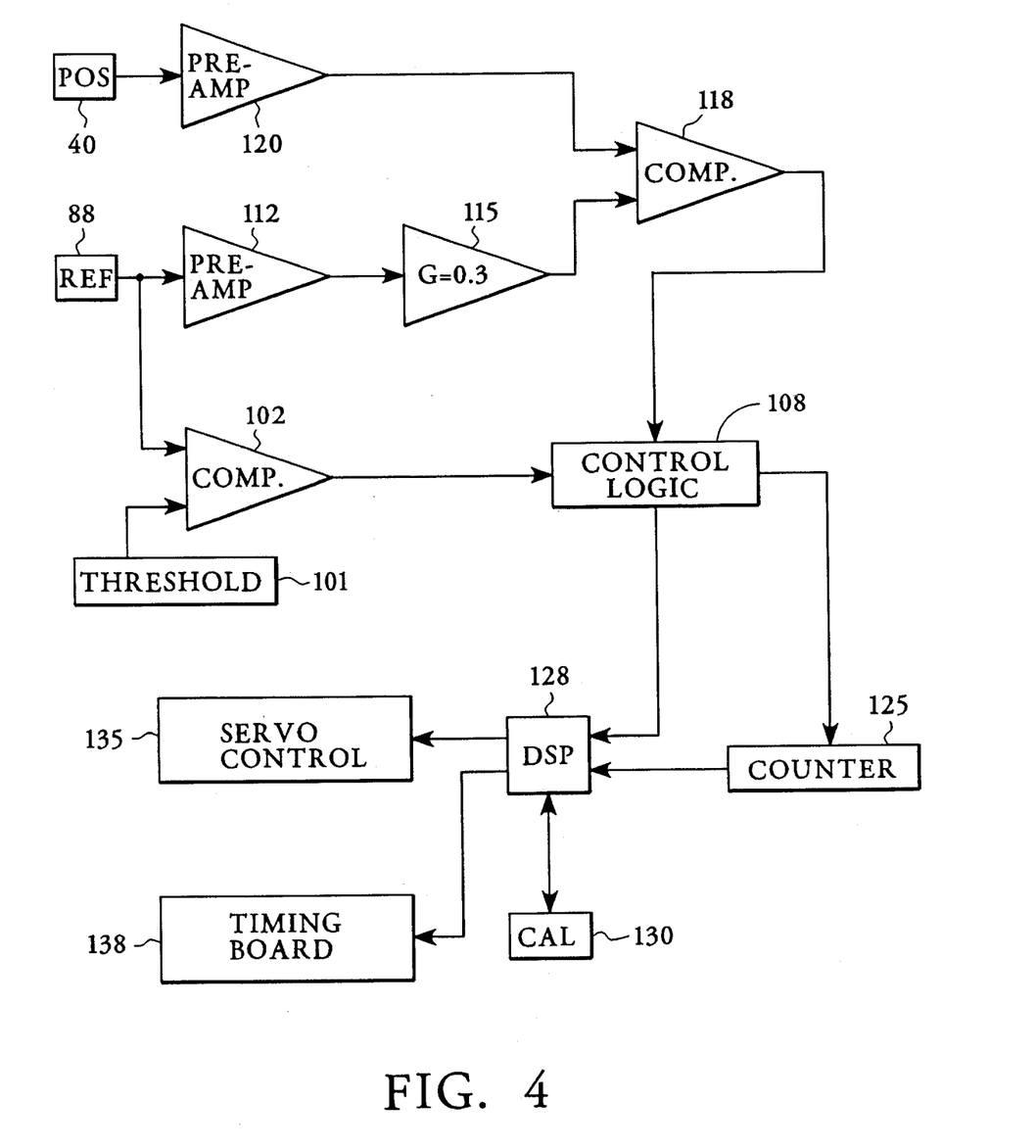
FIG. 4 is a block diagram of some of the electrical processing of the system of FIG. 3.

FIG. 4 offers an expanded view of the electronics involved in processing high frequency signals from the position detector 40 and the reference detector 88. A signal from the reference detector 88 is measured by the comparator 102, which is set to weed out noise by only transmitting an "on" signal to control logic 108 if the signal from the reference detector 88 is above a threshold level 101. The signal from reference detector 88 is separately received by a first preamp 112, and the amplified signal is sent to an amplifier 115 which outputs a signal that is 30% as large as the signal it received. This signal from amplifier 115 is received as an input to a second comparator 118, and is designed to set a level for identifying a pulse from the position detector by determining when the signal from the position detector is greater than a prescribed fraction of that from the reference detector 88. The second comparator 118 also receives an input signal from the position detector 40, after amplification by a second preamp 120 having an amplification generally matching the amplification of first preamp 112. Comparator 118 thus outputs a pulse that corresponds to the length of a light scan across the aperture 46 of the position detector 40.

The output of comparator 118 is received as an input to control logic 108. Also received as an input to control logic 108 is the output of comparator 102, which allows control logic 108 to differentiate between a true pulse from a light scan and optical noise. Control logic 108 outputs the true pulses to a counter 125 which counts the duration of each pulse. Control logic 108 also outputs the pulses to a digital signal processing chip (DSP) 128, which also receives information from the counter 125. DSP 128 can have a number of functions, including performing operations with the data from the pulses such as averaging, filtering, predictive filtering and statistical analysis. These operations would be performed after collecting information from a plurality of sweeps.

The DSP 128 also interacts with a calibration table 130 which has been calibrated with a micrometer or other known means of measuring a height of the surface 22 in order to correlate pulse width measurements with effective height of the surface 22. After correlating the pulse width from the counter 125 with the calibration table 130, information on the effective height of the surface 22 can be used to adjust that effective height. The DSP 128 can feed information on the effective height of the surface to a servo control 135 for the stage 65, so that the stage can adjust the effective height of the surface 22 during scanning. Alternatively, the DSP can feed information on the effective height of the surface to a timing board 138, which can use that information to calculate a corrected particle and/or pattern position on the surface 22 for all signals detected.

Figure 5:
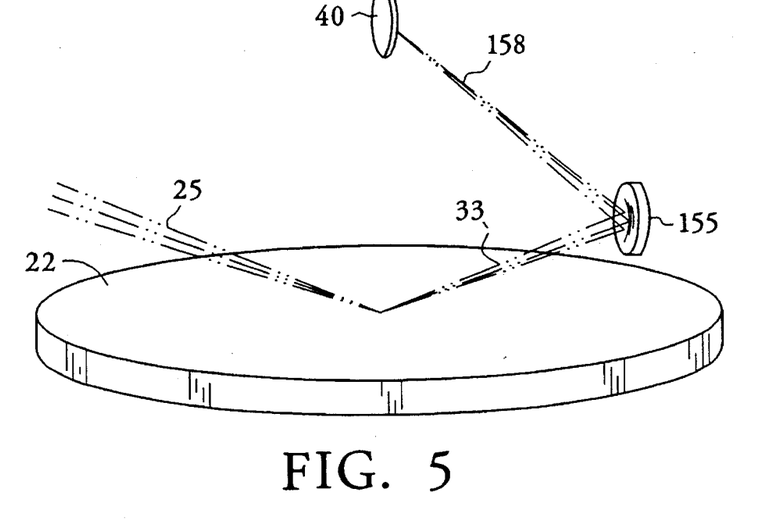
FIG. 5 is a diagram of an embodiment of the present invention employing a mirror for focusing the reflected beam.

FIG. 5 shows another embodiment of the present invention in which a mirror system 155 is disposed in the path of the specularly reflected beam 33. The mirror system 155 includes a concave reflective surface that focuses the reflected beam 33 much like a lens, but the mirror system 155 is oriented relative to the reflected beam 33 such that a mirrored beam 158 projects in a direction transverse to the reflected beam 33 as a result of reflection of the reflected beam 33 from the mirror system 155. As previously described for embodiments employing a lens for focusing the beam 33, a position detector 40 is located near an image plane of the mirror system 155, the position detector 40 sending a pulse to processing circuitry, not shown in this figure, which determines and corrects the effective height of the surface 22. At least one particle detector, also not shown in this figure, is positioned distal to the incident beam 25 and the reflected beam 33 to locate particles and/or patterns on the surface 22.

It should be noted that the mirror system 155 may include a planar instead of concave reflective surface, with a focusing lens disposed in the path of the mirrored beam 158 to image the surface 22 on the position detector 40. It should also be noted that in the previously described embodiments it is generally possible to replace a focusing lens with a focusing mirror, provided that the position detector is located at an image plane of the mirror rather than an image plane of the lens. Finally, the accuracy of the height detection system of the present invention is enhanced by minimizing mechanical vibrations of any of the components. As such, the wafer 20, lens 38 or mirror 155, and position detector 40 are positioned and connected in a fashion to minimize such vibrations. The accuracy is further enhanced by minimizing beam movements caused by air currents. This can be accomplished by enclosing the beam and other components appropriately, for example with tubing.

Figure 6:
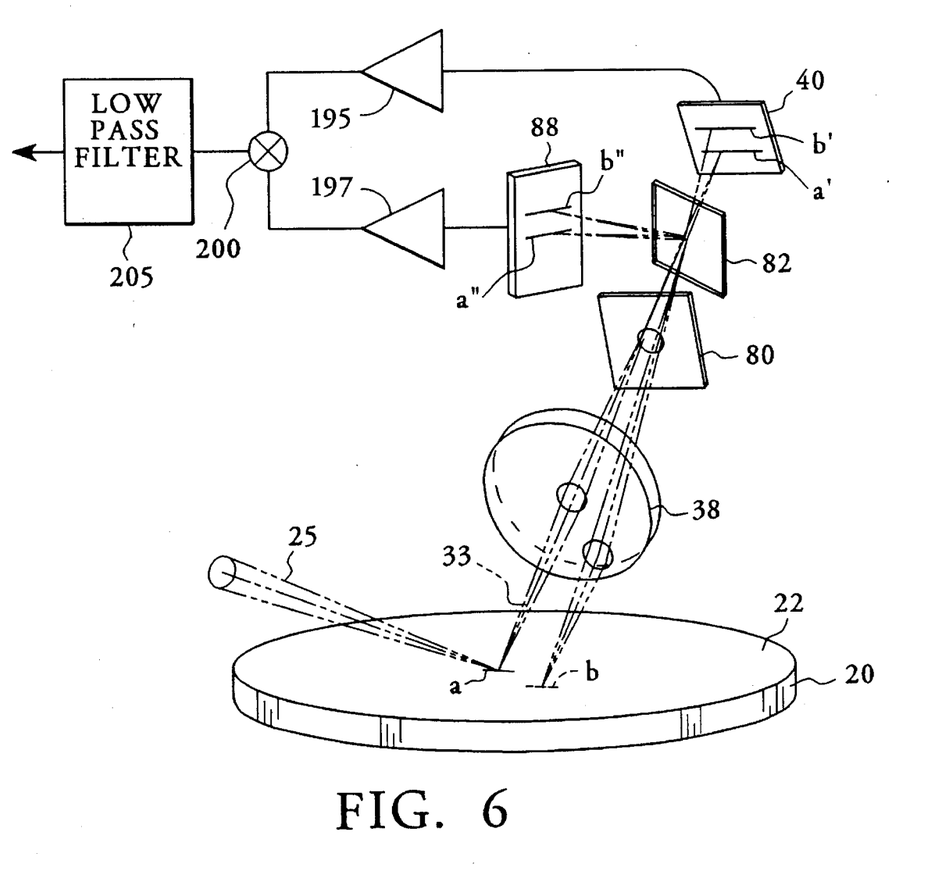
FIG. 6 is a diagram of a phase detection embodiment of the present invention.
Figure 7A:
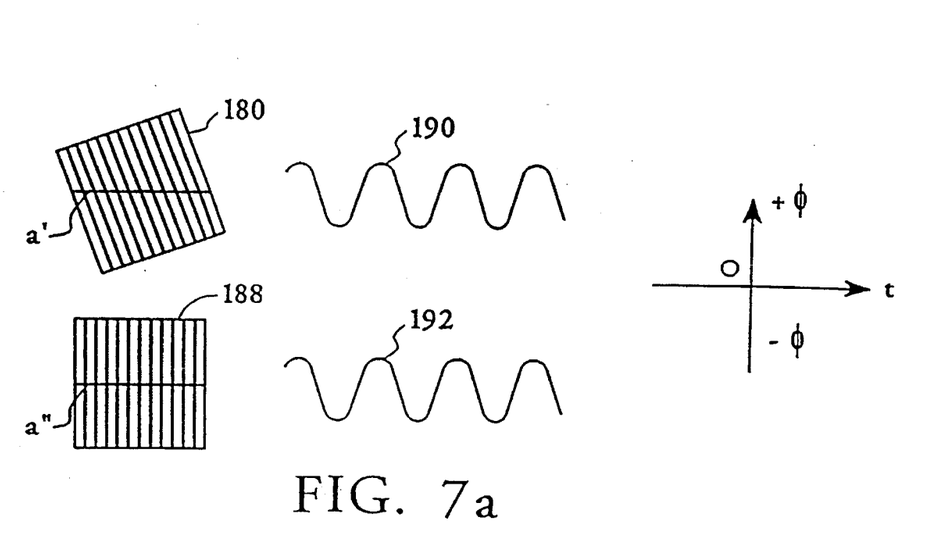
FIGS. 7a and 7b are diagram of periodic masks, output signals of photodetectors covered with those masks and phase changes detected with the embodiment of FIG. 6.
Figure 7B:
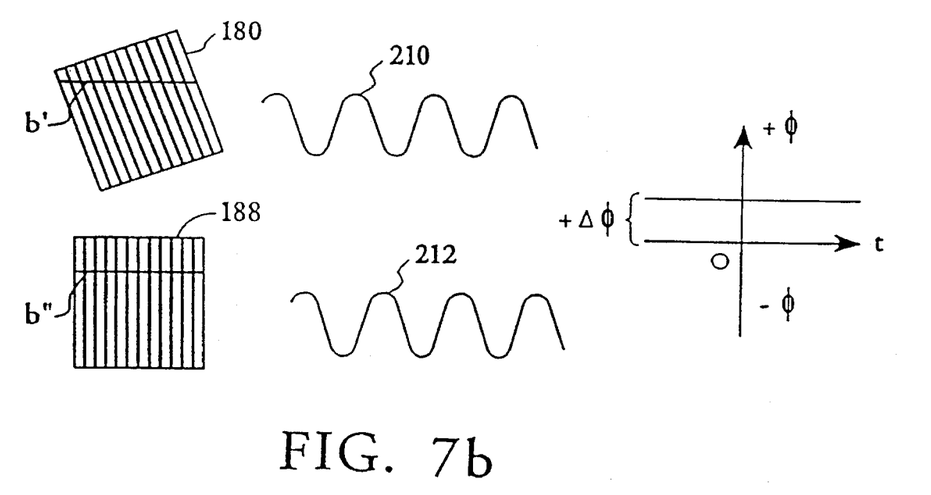

FIGS. 6,7a and 7b show an embodiment in which the position detector 40 and the reference detector 88 are both covered with masks with parallel lines forming gratings similar to diffraction gratings, but with the lines spaced apart substantially more than the size of the image spot so that diffraction effects are minimized. As before, an incident beam 25 impinging upon the surface 22 at an oblique angle is reflected as a reflected beam 33 that is focused by a lens 38. A spatial filter 80 is disposed near a Fourier transform plane of the lens 80, and a beam splitter 82 is positioned to direct a portion of the reflected beam 33 toward the position detector 40 and another portion of the reflected beam 33 toward the reference detector 88.

FIG. 7a and 7b shows the position detector and reference detector masks which, for clarity of illustration, were not shown in FIG. 6. The position detector 40 is covered with a positioning mask 180 that is comprised of a series of parallel, opaque lines that are separated by a similar series of open spaces. The masks can be conveniently formed by known photolithographic techniques. The reference detector 88 is likewise covered with a reference mask 188 that can be identical to the positioning mask but is oriented differently.

When the incident beam 25 is scanned across the surface 22 in a line (a) that corresponds to a desired height of the surface, an image (a') of the line (a) is formed upon the positioning mask 180 near the center of that mask 180, as shown in FIG. 7a. It is important that the lines of the positioning mask 180 are neither parallel nor perpendicular to the image line (a') of this embodiment. The reference mask 188 is impinged with another image line (a") which is focused near the center of that mask for the situation in which the surface is at the desired height, as shown in FIG. 7a. The lines of the reference mask 188 can be seen to be perpendicular to the line (a").

Due to the lines of the positioning mask 180, a signal 190 output by the position detector 40 will be periodic in time or distance. Similarly, the reference mask 188 causes the reference detector 88 to produce a periodic output signal 192. The signal 190 from the position detector 40 and the signal 192 from the reference detector 88, after amplification by preamps 195 and 197, can be fed to an exclusive OR gate or mixer 200, which compares the phase of the signals 190 and 192. The positioning mask 180 preferably has lines that are slightly thicker and spaced apart slightly more than the reference mask 188, in order to compensate for a geometric compression of the signal 190 due to the non-perpendicular traversal of the image (a') across positioning mask 180, as compared to the perpendicular traversal of reference mask 188 by image (a"). As can be seen in FIG. 7a, the signals 190 and 192 are in phase for this preferred height of the surface, which would send a signal, after passing through a low pass filter 205, to a control circuit, not shown, that would use the phase information to maintain the height of the surface unchanged.

Should the surface 22 be lower than the preferred height, so that the incident beam scans across the surface along line (b), an image (b') of that line (b) would be focused upon the positioning mask 180 above a center of that mask 180, as shown in FIG. 7b. The reference mask 188 will, in this case, also have an image (b") that is focused above the center of that mask 188. A signal 210 from the position detector 40 will be of the same period as the signal 190 from that detector 40 when the surface 22 was at the preferred height, but the signal 210 will be changed in phase throughout. On the other hand, a signal 212 generated by image (b") impinging upon the reference detector 88 after passing through the reference mask 188 will be unchanged in phase, as the lines of the mask 188 are perpendicular to the image (b"). By comparison of the signal 210 with a reference signal 212 in the exclusive OR gate or mixer 200, a phase difference Δφ can be obtained which can be used to reposition the surface 22 at the preferred height.

It should be noted that the fact that the signals 190 and 192 were in phase at the preferred surface 22 height and out of phase at another surface 22 height is arbitrary, as what is needed is simply a change in the phase difference between the signal from the reference detector 88 and the position detector 40 at different heights of the surface 22. It should also be noted that this embodiment has an advantage of having numerous, periodic pulse edges to compare with pulse edges of a periodic reference pulse. Due to this increase in the number of pulse edges, the accuracy of this embodiment for fine changes in height can be greater than that of an embodiment that compares a single pulse with a single reference pulse per scan.

One can see, however, that the graded aspect of the sensitivity of the position detector 40 in this embodiment is due to the slant of the lines of the positioning mask 188 compared with a direction that an image from the surface 22 varies with a variation in the height of the surface 22. Another way of looking at this is that the position detector 40 has a periodic sensitivity along a direction in which a location of the image changes with a change in the height of the surface, as well as having a periodic sensitivity in a direction transverse to the direction in which a location of the image changes with a change in the height of the surface. Thus a positive change in phase beyond a certain point may appear as a negative change in phase, resulting in a phase error. As such, the thickness and spacing of the lines of the mask 180, as well as the slant of those lines relative to a scan line, should be optimized to measure predicted variations in height of the surface 22 without encountering phase error.

Figures 8A, 8B, 9A:
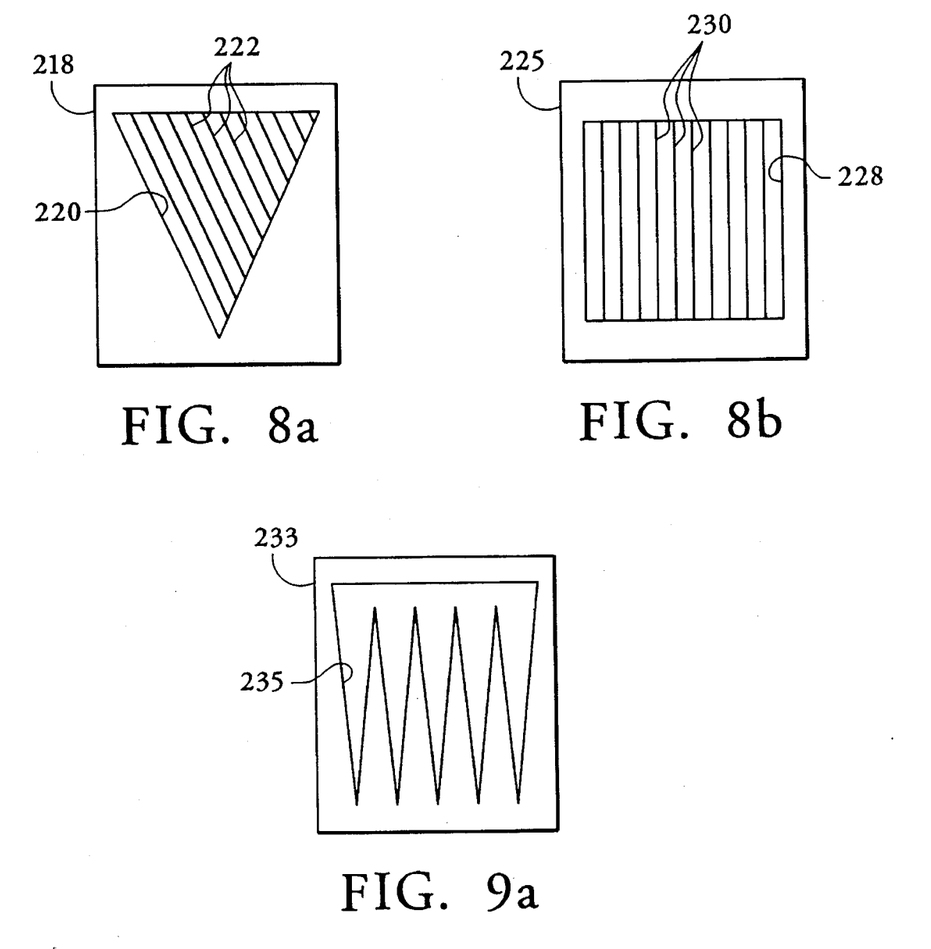
FIGS. 8a and 8b are a front view of position and reference detector masks used for an embodiment incorporating phase detection and graded sensitivity.
FIGS. 9a –9c are a front view of position detector masks incorporating graded sensitivity, waveforms and phase.

The use of mask 218 having a V-shaped aperture 220 in conjunction with a lined grating 222, as shown in FIG. 8, can eliminate phase error, as the pulse length across the V-shaped aperture can be measured and used to determined an approximate height of the surface 22, and a phase of a periodic pulse due to the grating 222 can be used to finely tune the measurement of the height of the surface 22. A position detector 40 covered with such a mask 218 can be used in conjunction with a reference detector 88 covered with a mask 225, shown in FIG. 8b, having a square aperture 228 and a grating 230 aligned with sides of the square aperture 228 so that the reference detector 88 can be used for a phase reference as well as to compensate for variations in intensity of the reflected beam 33. The output of this combination from repeated scans is thus similar to a signal of a given frequency that is modulated by a signal of another frequency.

Figure 9B:
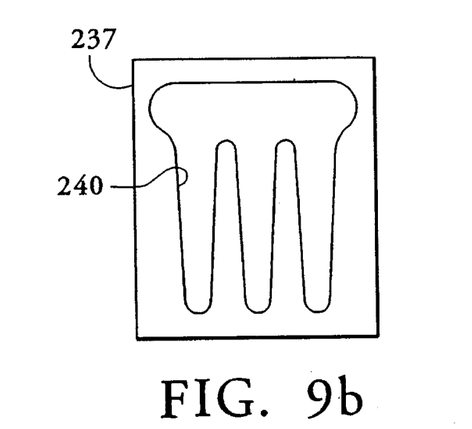
Figure 9C:
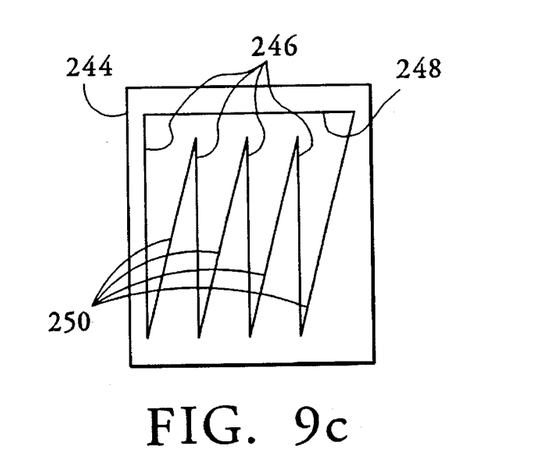

FIG. 9 shows a number of sawtooth-shaped or serpentine apertures for masks covering a photodetector to create a position sensor 40 having both periodic and graded sensitivity to light.

FIG. 9a shows mask 233 having a sawtooth edged aperture 235. An output of a photodetector covered with this mask 233 and impinged upon with an image of a scan line that traverses teeth of this mask 233 will vary in a both a graded and periodic fashion. The periodic variance can be seen to involve a change in phase of a leading edge of the periodic pulses and a change in phase of the trailing edge of the periodic pulses, either or both of which can be measured to calculate surface 22 height. Alternatively, a waveform of an output from a photodetector covered with this mask 233 can be seen to vary with a height of the surface 22, and this waveform can be used to measure and adjust the height of the surface 22.

FIG. 9b shows a mask 237 having an edge 240 defining a serpentine shaped aperture. This embodiment has the advantage that a small variation in image line height near a center of the mask, corresponding to a small perturbation from the preferred height of the surface 22, does not cause as significant a height compensating adjustment due to changed total pulse length, phase or waveform as does a small variation that is further removed from the preferred height. Thus oscillations about a preferred height are discouraged as the sinusoidal edge 240 of the aperture tends to cause the surface 22 to zero in on the preferred height.

FIG. 9c shows a mask 244 with a series of edges 246 defining an aperture 248 that are oriented so as to leave unchanged the phase of a leading or trailing edge of a wave signal from a scan line image that varies in the height with which it impinges upon the mask 244. On the other hand, another series of edges 250 defining the aperture 248 change phase as the scan line image changes in the height with which it traverses the mask 244. Thus the phase change of leading edges of the pulse can be compared with the phase change of trailing edges of the pulse to determine and adjust the height of the surface 22.

The invention has particular utility in a die to die comparison in a patterned wafer. In this situation, the scattered light detected by a particle detector 67, shown in FIG. 1, depends upon both the pattern and the presence or absence of a particle at a location on the surface. The presence or absence of a particle can be detected by comparing a signal from a detector 67 generated at the same location on a plurality of dies having identical patterns. For this case, it is important that the locations for which the signal is compared are identical. An error in the height of a surface of one die relative to another which can subvert this comparison can be corrected with the present invention.

We claim:

1. A system for detecting a height of a body to be optically inspected comprising, an incident beam of light directed obliquely at a surface of said body, said incident beam being at least partly reflected from said surface as a reflected beam, a scanning means for deflecting said incident beam across said surface in a line, a focusing means for focusing said reflected beam, and a first sensor disposed in a path of said reflected beam near an image plane of said surface formed by said focusing means, said sensor having a light sensitivity with a periodic variance along a direction transverse to said line and along which a position of an image of said line varies with a height of said surface, whereby a variation in said height of said surface results in a corresponding variation in phase, frequency or waveform of an output from said sensor.

2. The system of claim 1 further comprising, a reference second sensor with a periodic variance in light sensitivity, a beam splitter disposed in said path of said reflected beam and having means for diverting a first portion of said reflected beam toward said first sensor and a second portion of said reflected beam toward said reference second sensor, such that a first image of said line impinges upon said first sensor, and a second image of said line impinges upon said reference second sensor across a periodic variance in light sensitivity that is essentially unchanged along an orientation in which said second image of said line varies with said change in said height of said surface, and means for comparing an output of said position and said reference second sensor such that said height of said surface may be calculated.

3. The system of claim 2 wherein said periodic variance of said first sensor substantially matches said periodic variance of said reference second sensor.

4. The system of claim 2 wherein said first sensor comprises a photodetector and a mask defining an aperture adjoining the photodetector and disposed between said focusing means and said photodetector, said aperture spanned with lines and having a width oriented transversely to said direction.

5. The system of claim 1 wherein said first sensor comprises a photodetector and a mask defining a sawtooth edge adjoining the photodetector and disposed between said focusing means and said photodetector.

6. The system of claim 1 wherein said first sensor comprises a photodetector and a mask defining a serpentine edge adjoining the photodetector and disposed between said focusing means and said photodetector.

7. The system of claim 1 further comprising a plate defining a spatial filter disposed near a Fourier transform plane of said means for focusing said light.

8. The system of claim 1 further comprising a means for moving said surface in response to said variation of light detected by said first sensor.

9. A surface inspection system with height adjustment of the surface comprising, a signal responsive means for controlling a position of a body having a surface, means for impinging an incident beam of light at an oblique angle upon said surface, such that said incident beam is at least partly reflected from said surface as reflected light, means for focusing said reflected light at an image plane of said surface, a first detector disposed near said image plane, said first detector having a light sensitivity along a direction of said image plane wherein a location or an image of said surface varies with a change in a height of said surface, such that a signal from said first detector varies with said height, whereby said height of said surface may be determined and adjusted by said means for controlling said position of said body, and a surface feature detector disposed distal to said incident beam and said reflected light, whereby light from said incident beam that is scattered by a surface feature may be detected by said surface feature detector.

10. The system of claim 9 further comprising a spatial filter disposed near a Fourier transform plane of said means for focusing said reflected light.

11. The system of claim 9 further comprising, a beam splitter means for diverting part of said reflected light toward a reference second detector, means for comparing light detected by said first detector with light detected by said reference second detector, wherein variations in an intensity of said reflected light can be adjusted.

12. The system of claim 11 further comprising means for scanning said incident beam across said surface along a line transverse to an axis of said incident beam.

13. The system of claim 12 wherein said first detector comprises a photodetector and an opaque body defining an aperture adjoining the photodetector and disposed between said focusing means and said photodetector, said aperture having a width oriented transversely to said direction.

14. The system of claim 12 wherein said first detector has a periodic variance in light sensitivity transverse to said direction.

15. The system of claim 12 wherein said first detector has a periodic variance in light sensitivity transverse to said direction, and said reference second detector has a periodic variance in sensitivity substantially matching said periodic variance of said first detector and oriented such that an image of said surface impinges upon said reference second detector at a phase of said periodic variance that is essentially constant over different heights of said surface.

16. A method for detecting surface features with active surface realignment for surface inspection comprising, scanning an incident beam of light across a surface at an oblique angle, detecting a reflection of said incident beam such that an alignment of said surface and said beam is determined, detecting whether said incident beam is scattered, thereby determining whether a feature is located at a spot on said surface, and realigning said surface, during said scanning, such that a location of a spot on said surface may be more precisely determined.

17. The method of claim 16 wherein said detecting said reflection of said incident beam includes, orienting a first detector having a light sensitivity in a direction such that varying a height of said surface varies an output of said first detector, and focusing said reflection of said incident beam upon said first detector.

18. The method of claim 16 wherein said detecting said reflection of said incident beam includes detecting a location of said reflection upon said first detector.

19. The method of claim 17 wherein said first detector has a width along said direction and said detecting said reflection includes impinging said reflection on said first detector and timing a pulse generated by said first detector.

20. The method of claim 17 wherein said first detector has a light sensitivity that varies periodically transversely to said direction and said detecting said reflection of said incident beam includes impinging said reflection upon said first detector and measuring a wave output by said first detector.

21. The method of claim 17 further comprising, impinging a portion of said reflection upon a second reference detector, comparing a signal from said first detector with a signal from said reference second detector, and compensating said signal from said first detector based upon said signal from said reference second detector.

22. A system for detecting a height of a body, comprising, an incident beam of light directed obliquely at a surface of said body, said incident beam being at least partly reflected at a spot on said surface as a reflected beam, means for scanning said incident beam across said surface in a scan line;

a focusing means for focusing said reflected beam, and a sensor disposed in a path of said reflected beam near an image plane of said surface formed by said focusing means so that an image of at least a portion of the scan line is projected onto the sensor, wherein said sensor provides a pulsed signal whose width varies with a height of said surface.

23. The system of claim 22 further comprising:

a reference sensor;

a beam splitter disposed between said surface and said sensor and having means for diverting a portion of said reflected beam toward the reference sensor; and means for comparing light detected by said sensor with that from said reference sensor to compensate for intensity variations of said reflected beam.

24. The system of claim 22, wherein said sensor comprises:

a photodetector; and an aperture adjoining the photodetector and disposed between said focusing means and said photodetector, said aperture having a width oriented transversely to said direction and varying in value along said direction.

25. The system of claim 21, wherein said aperture comprises an opaque body defining a V-shaped mask hole therein, said hole having a top and a nadir, adjoining the photodetector and disposed between said focusing means and said photodetector, said top spaced from said nadir along said direction.

26. The system of claim 24, wherein said aperture is sawtooth-shaped or serpentine-shaped.

27. The system of claim 22, wherein said sensor comprises a photodetective face with a width oriented transversely to said direction and varying in value along said direction.

28. The system of claim 22, wherein said sensor has periodically variable light sensitivity transverse to said direction.

29. The system of claim 22, wherein said sensor comprises:

a photodetector; and a partly translucent filter adjoining the photodetector, said filter having a translucence that varies along said direction.

30. The system of claim 22, further comprising a plate defining a spatial filter disposed near a Fourier transform plane of said focusing means.

31. The system of claim 22 further comprising a means for moving said surface in response to said variation of light detected by said sensor.

32. The system of claim 22, wherein said direction is transverse to said surface.

33. A system for detecting a height of a body, comprising, an incident beam of light directed obliquely at a surface of said body, said incident beam being at least partly reflected at a line on said surface;

focusing means for focusing said at least part reflection of said incident beam to provide an image of said line; and a sensor disposed in a path of said focused reflection near an image plane of said surface formed by said focusing means so that an image of at least a portion of the line is projected onto the sensor, wherein said sensor provides a signal as a function of the length of said image projected onto the sensor, said length varying with a height of said surface.

34. A method for detecting a height of a body, comprising the steps of:

directing an incident beam of light obliquely at a surface of said body, said incident beam being at least partly reflected at a line on said surface;

focusing said at least part reflection of said incident beam to provide an image of said line; and sensing an image of at least a portion of the line in a path of said focused reflection near an image plane of said surface formed by said focusing step, and providing a signal as a function of the length of said at least a portion of the line, said length varying with a height of said surface.

35. A method for detecting a height of a body, comprising the steps of:

directing an incident beam of light obliquely at a surface of said body, said incident beam being at least partly reflected at a spot on said surface as a reflected beam;

scanning said incident beam across said surface in a scan line;

focusing said reflected beam; and sensing an image of at least a portion of the line in a path of said focused reflection near an image plane of said surface formed by said focusing step, and providing a pulsed signal whose width varies with a height of said surface.

* * * * *

UNITED STATES PATENT AND TRADEMARK OFFICE
CERTIFICATE OF CORRECTION

PATENT NO. : 5,576,831
DATED : November 19, 1996
INVENTOR(S) : Mehrdad Nikoonahad et al.

It is certified that error appears in the above-indentified patent and that said Letters Patent is hereby corrected as shown below:

In Formal Drawings:
    replace Figure 1 with Figure 1 attached.

In Column 13, line 40, in Claim 25:
    replace "The system of claim 21, wherein said aperture comprises" with:

--The system of claim 24, wherein said aperture comprises --

UNITED STATES PATENT AND TRADEMARK OFFICE
CERTIFICATE OF CORRECTION

PATENT NO. : 5,576,831
DATED : November 19, 1996
INVENTOR(S) : Mehrdad Nikoonahad et al It is certified that error appears in the above-identified patent and that said Letters Patent is hereby corrected as shown below:

The title page should be deleted and substitute therefor the attached title page:

The drawing sheet, consisting of figure 1, should be deleted to be replaced with the following drawing sheet consisting of fig. 1 as shown on the attached page.

Signed and Sealed this

Seventeenth Day of March, 1998

Attest:

BRUCE LEHMAN

*Attesting Officer*     *Commissioner of Patents and Trademarks*

United States Patent
Nikoonahad et al.

[11] Patent Number: 5,576,831
[45] Date of Patent: Nov. 19, 1996

[54] WAFER ALIGNMENT SENSOR

[75] Inventors: Mehrdad Nikoonahad, Menlo Park; James A. Tebelskis, San Jose, both of Calif.

[73] Assignee: Tencor Instruments, Santa Clara, Calif.

[21] Appl. No.: 263,203

[22] Filed: Jun. 20, 1994

[51] Int. Cl.⁶ .................................. G01B 11/00
[52] U.S. Cl. ........................ 356/375; 356/381; 356/237; 250/559.27; 250/559.31
[58] Field of Search .......................... 356/371, 375, 356/376, 381, 237, 73; 250/559.27, 559.31, 559.41

[56] References Cited

U.S. PATENT DOCUMENTS

| | | | |
|---|---|---|---|
| 3,667,846 | 6/1972 | Nater et al. | 356/371 |
| 4,405,238 | 9/1983 | Grobman et al. | 356/401 |
| 4,589,773 | 5/1986 | Ido et al. | 356/371 |
| 4,650,983 | 3/1987 | Suwa | 250/204 |
| 4,748,333 | 5/1988 | Mizutani et al. | 250/561 |
| 4,844,617 | 7/1989 | Kelderman et al. | 356/372 |
| 4,864,123 | 9/1989 | Mizutani et al. | 250/225 |
| 4,936,676 | 6/1990 | Stauffer | 356/375 |
| 5,162,642 | 11/1992 | Akamatsu et al. | 356/376 |
| 5,166,516 | 11/1992 | Kajimura | 250/234 |
| 5,272,517 | 12/1993 | Tokura | 356/375 |
| 5,298,976 | 3/1994 | Shahar et al. | 356/375 |

Primary Examiner—F. L. Evans
Attorney, Agent, or Firm—Majestic, Parsons Siebert & Hsue

[57] ABSTRACT

A surface height detection and positioning device for use in a surface inspection system. An incident beam of light impinges obliquely upon the surface, and a position detector is disposed to receive light reflected from the surface. The position detector has a sensitivity characteristic graded along a direction transverse to the surface, so that the output of the position detector is used to determine a height of the surface. The device can be incorporated into a particle detection system that scans patterned wafers with obliquely incident light to search for particles with a particle detector positioned to receive scattered light. In one embodiment, the position detector can have a width that is graded along the direction transverse to the surface, so that a scan line on the surface that is focused upon the position detector crosses the width of that detector in a time that varies as a function of the height of the surface. This time can be measured as an electrical pulse from the position detector that can be used for various purposes, including adjusting the height of the surface during scanning. In another embodiment, the position detector can have a periodic variance in light sensitivity that is graded, so that varying a height of the surface varies a phase of the output from the position detector.

35 Claims, 7 Drawing Sheets

FIG. 1